United States Patent [19] [11] 4,192,861
Micchelli et al. [45] Mar. 11, 1980

[54] HYDROCARBON PROPELLED AEROSOL HAIR SPRAY COMPOSITIONS

[75] Inventors: Albert L. Micchelli, Middletown; Frank A. Nowak, Jr., Somerville; Stuart H. Ganslaw, Morristown, all of N.J.

[73] Assignee: National Starch and Chemical Corporation, Bridgewater, N.J.

[21] Appl. No.: 903,441

[22] Filed: May 5, 1978

[51] Int. Cl.$^2$ .......................... A61K 7/00; A61K 9/00
[52] U.S. Cl. ........................................ 424/47; 424/70; 424/71; 424/78; 424/81; 424/325
[58] Field of Search .................... 424/47, 70, 71, 81

[56] References Cited

U.S. PATENT DOCUMENTS

| | | | |
|---|---|---|---|
| 2,996,471 | 8/1961 | Reiter et al. | 260/33.4 |
| 3,405,084 | 10/1968 | Bohac et al. | 260/29.6 |
| 3,577,517 | 5/1971 | Kubot et al. | 424/47 |
| 3,577,518 | 5/1971 | Sheppard et al. | 424/47 |
| 3,810,977 | 5/1974 | Levine et al. | 424/47 |

FOREIGN PATENT DOCUMENTS 1321836 7/1973 United Kingdom.

OTHER PUBLICATIONS

McCutcheon's Detergents & Emulsifiers, 1973 Ed., pp. 20 and 185.

Primary Examiner—Leonard Schenkman
Attorney, Agent, or Firm—Edwin Szala; Ellen T. Dec

[57] ABSTRACT

The solubility of hair spray resins derived from copolymers of unsaturated monocarboxylic acids and vinyl or vinylidene monomers in alcohol-hydrocarbon propellent systems is substantially increased by use of specific long chain amines as neutralizing agents therein.

8 Claims, No Drawings

HYDROCARBON PROPELLED AEROSOL HAIR SPRAY COMPOSITIONS

BACKGROUND OF THE INVENTION

I. Field of the Invention

The present invention is directed to novel aerosol hair spray compositions containing resins which are copolymers derived from unsaturated monocarboxylic acids and vinyl or vinylidene monomers wherein at least a portion of the available carboxylated functionalities are neutralized with specific long chain amines.

II. Brief Description of the Prior Art

Carboxylated vinyl polymeric hair spray resins, particularly the carboxylated acrylate, and/or acetate based resins, have long been favored for use in halocarbon-propelled aerosol hair spray formulations. In order to obtain optimum benefits for the use of such resins, it has been required to neutralize at least a portion of the available carboxyl functionalities with specific alkaline reagents, e.g. amines and aminohydroxy compounds, as described in, for example, U.S. Pat. Nos. 2,996,471; 3,405,084; 3,577,517, etc. Thus, alkaline reagents which are employed for such neutralizations include ammonia water, lithium hydroxide, potassium hydroxide, sodium hydroxide, mono-, di- or tri-ethanolamine, mono-, di or tripropanolamine, morpholine, amino ethyl ethanol amine, amino methyl propanol, amino methyl propanediol, hydroxy ethyl morpholine, ammonium salts of lysine or glycine and mixtures thereof. The purpose of this neutralization step is both to improve the water solubility or dispersibility of the resin thus permitting easy removal from the hair by merely washing with shampoo and also to affect the degree of flexibility of the resultant film when sprayed on the hair (i.e. to produce a soft film, normal film or a film suitable for "hard to hold" hair). Additionally, British Pat. No. 1,321,836 has taught the use of primary amines containing 4 to 16 carbon atoms together with the alkanolamines described hereinabove for the neutralization of specific polymers in halocarbon propelled systems. The polymers described therein must be free from chromophoric groups and amide groups and consist of copolymers of unsaturated dicarboxylic acids and a vinyl or vinylidene monomer.

Recent ecological considerations have resulted in a shift from the use of halocarbons towards the use of certain hydrocarbons as propellents in aerosol hair spray formulations. However, the use of hydrocarbon propellents poses a number of problems, some of which are related to the decreased solubility of the hair spray resins in the alcohol-hydrocarbon systems. Thus, although the commercially favored carboxylated resins are soluble in the anhydrous alcohol-halocarbon systems, their reduced solubility in the proposed alcohol-hydrocarbon propellent may render the use thereof unacceptable to the industry.

SUMMARY OF THE INVENTION

It has now been found that the use of specific long chain amines instead of the conventionally employed amines mentioned above for the neutralization of hair spray resins consisting of a copolymer of unsaturated monocarboxylic acids and vinyl or vinylidene monomers substantially increases the solubility of the resins in the alcohol hydrocarbon propellent systems.

Novel aerosol hair spray formulations in aerosol containers are therefore produced comprising 0.5 to 5% by weight of a resin consisting of a copolymer of at least one unsaturated monocarboxylic acid and at least one vinyl or vinylidene monomer, 5–60% hydrocarbon propellent with solvent comprising the remainder of said composition (to 100%) wherein neutralization of the available carboxyl groups is effected with a long chain amine containing eight to twenty carbon atoms.

The present invention is also directed to an improved process for the preparation of aerosol hair spray formulations in aerosol containers wherein the formulation comprises 0.5 to 5% by weight of a resin consisting of a copolymer of at least one unsaturated monocarboxylic acid and at least one vinyl or vinylidene monomer, 5–60% hydrocarbon propellent and solvent (to 100%) and wherein at least a portion of the available carboxyl groups are neutralized, the improvement which comprises neutralizing the carboxyl functionalities with a long chain amine containing eight to twenty carbon atoms thereby substantially increasing the solubility of the resin.

DETAILED DESCRIPTION OF THE PREFERRED EMBODIMENTS

The present invention is equally applicable to use with any of the conventionally employed hair spray resins consisting of a copolymer of unsaturated monocarboxylic acids and vinyl or vinylidene monomers. Such resins generally comprise organic vinyl polymers containing:

(i) 5–55 mole percent monocarboxylic acid monomer such as a monomer selected from the group consisting of acrylic acid, methacrylic acid, crotonic acid, allyl acetic acid, 2-allyl oxypropionic acid, beta-benzoyl acrylic acid, 2-furfural acrylic acid, 2-vinyl propionic acid, vinylacetic acid, sorbic acid and mixtures thereof; and (ii) 45–95 mole percent of at least one monomer selected from the group consisting of:
  (a) styrene and derivatives thereof,
  (b) methacrylate and acrylate alkyl esters wherein the alkyl group contains 1 to 18 carbon atoms,
  (c) vinyl esters of the formula $CH_2=CH-OCOR$ where R is an alkyl group containing 1–18 carbon atoms,
  (d) alkyl substituted acrylamides and methacrylamides of the formula $CH_2=CR-CONR_1R_2$ where R is H or $CH_3$; $R_1$ is H or $C_1-C_{12}$ and $R_2$ is $C_1-C_{18}$,
  (e) diesters of fumaric, itaconic and maleic acids, and,
  (f) vinyl ethers such as methyl vinyl ether, isobutyl vinyl ether, etc.

In addition to the two monomeric components described above, the carboxylated resin polymer may also contain up to about 30 mole percent of at least one of the following functional monomers:

(a) hydroxy functional acrylates and methacrylates such as hydroxy ethyl acrylate, hydroxy propyl acrylate, hydroxy ethyl methacrylate, etc.
(b) cationic monomers such as t-butyl aminoethyl methacrylate, dimethyl aminoethyl methacrylate, diethyl aminoethyl methacrylate and the quaternized derivatives thereof such as the quaternized product of 1-chloromethacrylate and trimethylamine or of dimethylaminoethyl methacrylate and dimethyl sulfate;
(c) acrylamide and non-alkyl substituted acrylamides such as diacetone acrylamide;
(d) cyclic amides such as vinyl pyrrolidone.

Exemplary of such hair spray resins are the vinyl acetate-crotonic acid copolymers and carboxylated terpolymers of vinyl acetate, crotonic acid and a vinyl ester of an alpha-branched saturated aliphatic monocarboxylic acid containing from 5 to 10 carbon atoms in the carboxylic acid moiety (the latter two resins are respectively described in U.S. Pat. Nos. 2,996,471 and 3,810,977, the disclosures of which are incorporated herein by reference and are available from National Starch and Chemical Corporation under the RESYN trademark); interpolymers of alkyl acrylamide, acrylamide or methacrylamide, N-vinyl pyrrolidone and acrylic or methacrylic acid (e.g. QUADRAMER, a trademark of American Cyanamid Co.); copolymers of N-tert-octylacrylamide, methyl methacrylate, hydroxypropyl methacrylate, acrylic acid and t-butyl aminoethyl methacrylate sold by National Starch and Chemical Corporation under the AMPHOMER trademark; partially hydrolyzed copolymers of acrylic ester with other vinyl monomers (e.g. CIBA 325); terpolymers of vinyl type monomers containing carboxylic groups (e.g. VEM 640-B from the Barr Co.); the interpolymers of various alkyl methacrylates and acrylic acid (e.g. Resin E-1139 available from Rohm and Haas); etc.

In accordance with the present invention, the particular hair spray resin is reacted with a long chain amine to neutralize at least a portion of the available carboxyl functionalities. Long chain amines suitable for use herein comprise those primary, secondary and tertiary amines containing from 8 to 20, preferably 12–18, carbon atoms and include octadecyl amine, octyl amine, hexadecyl amine, cocoamine, dimethyloctadecylamine, stearyl amine, etc. If desired, a minor portion (i.e. generally less than about 50%) of the carboxyl groups which are to be neutralized may be neutralized with the amines or alkanolamines of the prior art for reasons of economy, availability, etc.; however, such formulations may be characterized by a reduction in the solubility improvements obtained herein.

The neutralization step is generally carried out in one of two ways. The neutralizing agent can be dissolved in the solvent system and then the resin added thereto. Alternatively, the resin may be dispersed in the solvent system with the neutralizing agent added thereafter. In either case, mixing is continued until solution is complete with heat employed, if desired, to facilitate solution.

Generally, 7 to 100% of the available carboxyl groups are neutralized with the actual degree of neutralization required depending primarily upon the specific resin employed. Thus, the copolymer of octylacrylamide, methyl methacrylate, hydroxypropyl methacrylate, acrylic acid and butylaminoethyl methacrylate is generally neutralized to an extent of 70–90% while the interpolymers of alkyl acrylamide, acrylamide or methacrylamide, N-vinyl pyrrolidone and acrylic or methacrylic acid are neutralized to only about 7%. As will be recognized by one skilled in the art, the amount of neutralizing agent required will be approximately equimolar to the percent of the carboxyl groups to be neutralized.

Solvents suitable for use in the aerosol hair spray formulations of the present invention include methanol, ethanol, propanol, and butanol alone or in combination with 0.1–10% of water or 1–35% of other conventional cosolvents e.g. methylene chloride, trichloroethylene, and methyl cellosolve.

Suitable hydrocarbon propellents which may be employed in the present formulation include, for example, propane, isobutane, n-butane, 2,2-dimethyl propane, isopentane and mixtures thereof, used in amounts of 5 to 60%. Among the most commonly employed propellent mixtures is Propellent A46, a blend of propane and butanes.

Optional additives may be incorporated into the aerosol formulations of this invention in order to modify certain properties thereof. Among these additives may be included: plasticizers such as glycols, phthalate esters and glycerine; silicones, emollients, lubricants and penetrants such as lanolin compounds; protein hydrolyzates and other protein derivatives; ethylene oxide adducts and polyoxyethylene cholesterol; dyes, tints, and other colorants; and perfumes.

In general, the formulations of the present invention can be prepared by merely dissolving the resin in the solvent system, adding the neutralizing agent, as well as any modifying agents, and then charging this "concentrate" into the aerosol container. The desired propellent is then added in liquid form under pressure in accordance with conventional techniques.

With regard to proportions, the final aerosol formulations typically contain the monocarboxylated hair spray resin which has been neutralized with the long chain amine to the degree desired, in a concentration of from 0.5 to 5.0% by weight, preferably 1.0–3.0%; hydrocarbon propellent in an amount of 5 to 60%, preferably 20 to 40% by weight with the solvent comprising the remainder of the composition (to 100%). It should be recognized that the latter proportions should be considered as being merely illustrative inasmuch as it may well be possible to prepare operable formulations having concentrations of components which fall outside the above suggested ranges.

The resulting hair fixing formulations exhibit all of the characteristics required of such a product, resulting in films which hold the hair well and which are easily removed by shampooing.

In the following examples, which further illustrate this invention, all parts given are by weight unless otherwise indicated.

EXAMPLE I

This example illustrates the preparation of an aerosol hair spray formulation representative of the present invention and the improvement in solubility obtained thereby.

Various samples were prepared, each of which contained two parts of a monocarboxylated resin available from National Starch and Chemical Corp. under the tradename AMPHOMER and comprising a copolymer of N-tert-octylacrylamide, methyl methacrylate, hydroxypropyl methacrylate, acrylic acid and t-butyl aminoethyl methacrylate which were neutralized with a variety of long chain amines as shown in Table I. As a control, a sample was also prepared using a molar equivalent proportion of 2-amino-2-methyl-1-propanol in accordance with prior art techniques. In each case sufficient molar amounts of amine were used to neutralize approximately 90% of the available carboxyl groups. The neutralized resin was then dissolved in anhydrous alcohol, and the concentrate and propellent added to a glass aerosol vessel fitted with a thermocouple device. The filled vessels were chilled slowly until turbidity (signifying resin insolubility) developed. The resultant "cloud point," i.e. the temperature at which the polymer can be seen to precipitate from the solution, was recorded. A lower cloud point indicates better solubility.

TABLE I

|   | 1 | 2 | 3 | 4 | 5 |
|---|---|---|---|---|---|
| AMPHOMER | 2.00 | 2.00 | 2.00 | 2.00 | 2.00 |
| 2-Amino-2-methyl-1-propanol (control) | 0.33 | x | x | x | x |
| Octadecyl amine | x | 1.02 | x | x | x |
| Octyl amine | x | x | 0.53 | x | x |
| Dimethyloctadecylamine | x | x | x | 1.15 | x |
| Cocoamine* | x | x | x | x | 0.75 |
| Anh. ethanol | 42.67 | 41.98 | 42.47 | 41.85 | 42.25 |
| Propellent A-46** | 55.00 | 55.00 | 55.00 | 55.00 | 55.00 |
|   | 100.00 | 100.00 | 100.00 | 100.00 | 100.00 |
| Cloud point (°C.) | >20° | <−30° | −25° | <−30° | <−30° |

*Typical chain length distribution  7.0% caprylyl $C_8$
Apparent molecular weight = 204  6.5% capryl $C_{10}$
53.0% lauryl $C_{12}$
19.0% myristyl $C_{14}$
8.5% palmityl $C_{16}$
1.0% stearyl $C_{18}$
5.0% allyl-unsaturated $C_{18}$
**A commercially available 90/10 blend of butanes and propane.

As is shown by the observed results, the use of the long chain amines in the neutralization of monocarboxylated hair spray resins substantially improves the solubility of the resin in the aerosol system thereby permitting use of relatively large quantities of the hydrocarbon propellent.

EXAMPLE II

This example further illustrates the improved polymer solubility obtained using long chain amines as neutralizing agents for RESYN 28-2930, a monocarboxylated resin available from National Starch and Chemical Corp. and comprising a terpolymer of vinyl acetate, crotonic acid and vinyl neodecanoate.

The formulations were prepared in accordance with the method described in Example I and the compositions and cloud points shown in Table II.

TABLE II

|   | 1 | 2 | 3 | 4 | 5 |
|---|---|---|---|---|---|
| RESYN 28-2930 | 2.0 | 2.0 | 2.0 | 2.0 | 2.0 |
| Stearyl amine | x | 0.32 | 0.64 | x | 0.32 |
| 2-Amino-2-methyl-1-propanol | 0.2 | 0.1 | x | 0.2 | 0.1 |
| Isopropanol | 57.8 | 57.58 | 57.36 | 67.80 | 67.58 |
| Propellant A-46 | 40.0 | 40.00 | 40.00 | 30.00 | 30.00 |
|   | 100.00 | 100.00 | 100.00 | 100.00 | 100.00 |
| Cloud point (°F.) | >75° | >75° | 54° | >75° | 60° |

The results presented above show the increase in solubility observed when stearyl amine is used as the neutralizing agent for the monocarboxylated hair spray resins in accordance with the present invention.

EXAMPLE III

The basic procedure described in Example I was repeated using RESYN 28-1310 (a monocarboxylated resin comprising a copolymer of vinyl acetate and crotonic acid available from National Starch and Chemical Corp.) together with a variety of long chain amines used to neutralize approximately 90% of the available carboxyl groups. The formulations and corresponding cloud points are shown in Table III.

TABLE III

|   | 1 | 2 | 3 | 4 | 5 |
|---|---|---|---|---|---|
| RESYN 28-1310 | 2.00 | 2.00 | 2.00 | 2.00 | 2.00 |
| Octadecylamine (C-18) | 0.58 |   |   |   |   |
| Octylamine (C-8) |   | 0.30 |   |   |   |
| Cocoamine |   |   | 0.43 |   |   |
| Hexadecyl amine (C-16) |   |   |   | 0.51 |   |
| 2-Amino-2-methyl-1-propanol (control) |   |   |   |   | 0.18 |
| Anhydrous ethanol | 82.42 | 82.70 | 82.57 | 82.49 | 82.82 |
| Propellent A-46 | 15.00 | 15.00 | 15.00 | 15.00 | 15.00 |
|   | 100.00 | 100.00 | 100.00 | 100.00 | 100.00 |
| Cloud point (°F.) | 20° F. | 30° F. | 8° F. | 10° F. | 40° F. |

Again, substantially improved polymer solubility results were obtained in the samples which were neutralized with long chain amines in accordance with the present invention.

EXAMPLE IV

This example illustrates the improved solubility obtained using stearyl amine as neutralizing agent for the AMPHOMER resin used in Example I in the isopropanol-methylene chloride co-solvent systems shown in Table IV.

TABLE IV

|   | 1 | 2 | 3 |
|---|---|---|---|
| AMPHOMER | 2.0 | 2.0 | 2.0 |
| Stearyl amine | — | 0.5 | 1.0 |
| 2-Amino-2-methyl-1-propanol | 0.33 | 0.16 | — |
| Methylene chloride | 5.0 | 5.0 | 5.0 |
| Isopropanol | 42.67 | 42.34 | 42.0 |
| Propellent A-46 | 50.00 | 50.00 | 50.00 |
|   | 100.00 | 100.00 | 100.00 |
| Cloud point (°F.) | >75° | >75° | −20° |

The results observed above show the improved solubility obtained using the long chain amine neutralizing agents as disclosed herein in complete replacement for the prior art neutralizing agents thus permitting use of high levels of propellent.

Summarizing, it is illustrated by the examples presented herein that the neutralization of monocarboxylated vinyl hair spray resins with long chain amines containing 8 to 20 carbon atoms substantially increases the solubility of the resin hydrocarbon propelled aerosol hair spray formulations.

Variations may be made in proportions, procedures, and materials without departing from the scope of the invention as defined by the following claims.

We claim:

1. Aerosol hair spray compositions in aerosol containers, said compositions comprising 0.5 to 5% by weight of a resin consisting of a copolymer of at least one unsaturated monocarboxylic acid and at least one vinyl or vinylidene monomer, 5-60% hydrocarbon propellent, with solvent comprising the remainder of said composition (to 100%), wherein 7 to 100% of the available carboxyl groups of said resin are neutralized, depending on the type of resin employed, with at least 50% of the carboxyl groups which are to be neutralized being neutralized with a long chain primary, secondary or tertiary amine, wherein the longest chain of the amine contains 8 to 20 carbon atoms, the amount of neutralization being such that the solubility of the resin is substantially increased.

2. Claim 1 wherein the resin contains:

(i) 5–55 mole percent monocarboxylic acid monomer selected from the group consisting of acrylic acid, methacrylic acid, crotonic acid, allyl acetic acid, 2-allyl oxypropionic acid, beta-benzoyl acrylic acid, 2-furfural acrylic acid, 2-vinyl propionic acid, vinylacetic acid, sorbic acid and mixtures thereof; and (ii) 45–95 mole percent of at least one monomer selected from the group consisting of:
  (a) styrene and derivatives thereof,
  (b) methacrylate and acrylate alkyl esters wherein the alkyl group contains 1 to 18 carbon atoms,
  (c) vinyl esters of the formula $CH_2=CH-OCOR$ where R is an alkyl group containing 1–18 carbon atoms,
  (d) alkyl substituted acrylamides and methacrylamides of the formula $CH_2=CR-CONR_1R_2$ where R is H or $CH_3$; $R_1$ is H or $C_1-C_{12}$ and $R_2$ is $C_1-C_{18}$,
  (e) diesters of fumaric, itaconic and maleic acids, and,
  (f) vinyl ethers; and (iii) 0–30 mole percent of at least one monomer selected from the group consisting of:
  (a) hydroxy functional acrylates and methacrylates,
  (b) cationic monomers selected from the group consisting of t-butyl aminoethyl methacrylate, dimethyl aminoethyl methacrylate, diethyl aminoethyl methacrylate, and the quaternized derivatives thereof,
  (c) acrylamide and non-alkyl substituted acrylamides, and
  (d) cyclic amides.

3. Claim 1 wherein the resin is a copolymer of vinyl acetate and crotonic acid.

4. Claim 1 wherein the resin is a terpolymer of vinyl acetate, crotonic acid and a vinyl ester of an alpha-branched saturated aliphatic monocarboxylic acid containing from 5 to 10 carbon atoms in the carboxylic acid moiety.

5. Claim 1 wherein the resin is a copolymer of N-tert-octylacrylamide, methyl methacrylate, hydroxypropyl methacrylate, acrylic acid and t-butyl aminoethyl methacrylate.

6. Claim 1 wherein the hydrocarbon propellent is a blend of butanes and propane.

7. Claim 1 wherein the long chain amine is selected from the group consisting of octadecyl amine, octyl amine, hexadecyl amine, cocoamine, dimethyloctadecylamine and stearyl amine.

8. Claim 1 wherein a minor portion of the carboxyl groups which are to be neutralized are neutralized with an amine or alkanolamine selected from the group consisting of ammonia water, mono-, di- or triethanolamine, mono-, di or tri-propanolamine, morpholine, amino ethyl ethanol amine, amino methyl propanol, amino methyl propanediol, hydroxy ethyl morpholine, ammonium salts of lysine or glycine and mixtures thereof.

* * * * *